US005267558A

United States Patent [19]

Haertle et al.

[11] Patent Number: 5,267,558

[45] Date of Patent: Dec. 7, 1993

[54] CHEMICAL CARTRIDGE FOR RESPIRATORS

[75] Inventors: Klaus Haertle; Volker Hunnebeck; Karl-Heinz Kohricht; Michael Schwichtenberg; Stefan Zloczysti, all of Berlin, Fed. Rep. of Germany

[73] Assignee: Auergesellschaft GmbH, Berlin, Fed. Rep. of Germany

[21] Appl. No.: 928,985

[22] Filed: Aug. 12, 1992

[30] Foreign Application Priority Data

Aug. 13, 1991 [DE] Fed. Rep. of Germany ....... 4126685

[51] Int. Cl.[5] ........ A61M 15/00

[52] U.S. Cl. ........ 128/202.26; 128/205.12

[58] Field of Search ........ 128/202.26, 205.12, 128/205.28

[56] References Cited

U.S. PATENT DOCUMENTS 2,106,393 1/1938 Hausmann ........ 128/205.28
3,794,030 2/1974 Cotabish et al. ........ 128/202.26
4,086,923 5/1978 Henkin ........ 128/205.12
4,277,443 7/1981 Van der Smissen et al. ... 128/202.26

FOREIGN PATENT DOCUMENTS 2635376 2/1978 Fed. Rep. of Germany .

*Primary Examiner*—Edgar S. Burr
*Assistant Examiner*—Aaron J. Louis
*Attorney, Agent, or Firm*—Reed, Smith, Shaw & McClay

[57] ABSTRACT

A chemical cartridge for respirators for respirators, the cartridge containing a chemical, e.g., potassium hyperoxide, which when acted upon by carbon dioxide and moisture, produces oxygen from a stream of inhaled air. Two discharge nozzles are provided which project into the chemical and out of which the regenerated exhaled air flows. The incoming flow occurs over a large area and the outflow occurs over a small area with the peripheral surfaces of the discharge nozzles being spaced substantially equidistant from an inlet surface of the chemical, thereby ensuring optimum use of the chemical for oxygen production purposes because a user's exhaled air is caused to flow completely through the entire space occupied by the chemical.

7 Claims, 1 Drawing Sheet

CHEMICAL CARTRIDGE FOR RESPIRATORS

FIELD OF THE INVENTION

The present invention relates in general to respiratory equipment and, in particular, to a chemical cartridge for respirator apparatus wherein the cartridge comprises a chemical that reacts with carbon dioxide and water vapor exhaled by a user to yield oxygen to be inhaled by the user.

BACKGROUND OF THE INVENTION

Chemical cartridges containing suitable compounds which react with a user's expiratory gases and water vapor to yield breathable oxygen are known. A chemical cartridge of this type is disclosed in German patent Document DE 26 35 376 C2 wherein the reactive chemical in the cartridge is bounded by an upper and a lower chamber. In operation, a user's exhaled air is caused to flow through an end face of the chemical adjacent the upper chamber. Once inside the chemical mass, the exhaled air is converted into breathable air that flows into a respirator bag through a single perforated discharge tube situated in a central region of the chemical.

A disadvantage of such a construction arises due to the location of the discharge tube. That is, because the discharge tube is disposed in the center of the space occupied by the chemical, peripheral portions of the chemical, particularly in the vicinity of the lower chamber, are not completely flowed through or contacted by the exhaled air. As a consequence, the chemical is not utilized to optimum efficiency.

An advantage exists, therefore, for a chemical cartridge for use in respiratory equipment which converts a user's exhaled air into breathable air, wherein all regions of the chemical, including peripheral portions thereof, are efficiently flowed through and contacted by the exhaled air so as to effect complete utilization of the chemical for oxygen production purposes.

SUMMARY OF THE INVENTION

The present invention provides an improved chemical cartridge for respirators, the cartridge comprising a chemical which combines with carbon dioxide and water vapor from a user's exhaled air to yield oxygen. In operation, the user's exhaled air is caused to flow through an end face and a generated circumferential surface of the volume occupied by the chemical. Within the mass of chemical, the exhaled air is converted into breathable air that flows into a respirator bag through a pair of perforated, tubular discharge nozzles. The discharge nozzles are so constructed and arranged that their peripheral surfaces are equidistant or substantially equidistant from the boundary surface comprising the end face and generated circumferential surface through which the exhaled air enters the chemical mass.

An advantage of above-described chemical cartridge construction is that a predetermined quantity of chemical defined by the volume of the chemical mass is fully utilized for oxygen production purposes, thereby effecting maximum service life in a respirator incorporating such cartridge.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
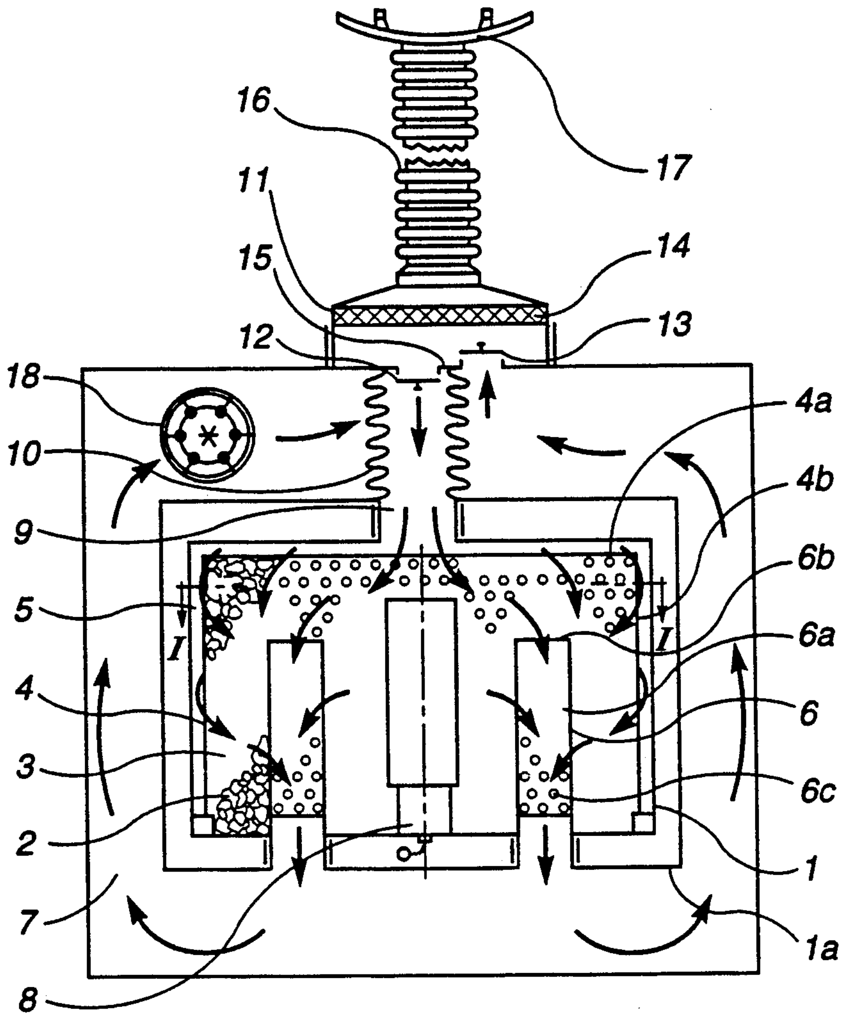
FIG. 1 is an elevation view, in partial section, of a first preferred embodiment of the chemical cartridge according to the present invention.

FIG. 1 depicts a respirator apparatus which operates on recycled air, i.e., the apparatus converts carbon dioxide and water vapor contained in air exhaled by a user of the apparatus into breathable oxygen which may be inhaled by the user. The respirator apparatus includes a chemical cartridge 1 constructed in accordance with the present invention. The cartridge, comprises a casing containing a chemical 2 such as, for example, potassium hyperoxide, which when acted upon by carbon dioxide and moisture borne by the user's exhaled air stream, produces oxygen to be inhaled by the user.

A respirator bag 7 is disposed around and spaced at a distance from the chemical cartridge 1 so as to envelope the cartridge. Reference numeral 9 denotes an opening through which exhaled air may flow into the chemical cartridge 1. One end of a first breathing tube 10 is connected to the inflow opening 9 and the other thereof is connected to a casing 11 in which are disposed an exhaled-air valve 12, an inhaled-air valve 13 and a heat exchanger 14. In addition to the chemical cartridge 1, the respirator bag also surrounds the first breathing tube 10 and has an inhaled and exhaled air opening 15 that is connected to the casing 11. A second breathing tube 16 is secured at one end to the casing 11 and at its other end carries a mouthpiece 17. The respirator bag 7 also is provided with a valve 18 for relieving excess pressure that may occur in the bag as a result the user's respiratory activity.

Figure 2:
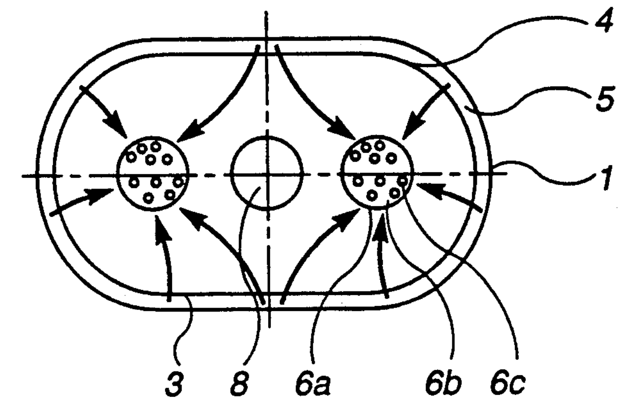
FIG. 2 is a view taken along line I—I of FIG. 1.

Viewing FIGS. 1 and 2 together reveals that the mass of chemical 2 is disposed in an insert 3, preferably of oval cylindrical configuration. The insert is formed of screen material and comprises an end face **4*a* and a generated circumferential wall surface 4*b*. Insert 3 substantially bounds the exterior of the space or volume occupied by the chemical and defines an inlet surface 4 through which exhaled air passes into the chemical. Insert 3 is positioned in cartridge 1 such that its open side faces a base surface la of cartridge 1. A continuous duct 5 for exhaled air is formed between the inner walls of the cartridge casing and the end face 4*a* and the generated surface 4*b* of insert 3. Two tubular discharge nozzles 6 are disposed on the base surface 1*a* of cartridge 1. Each nozzle has an elongated portion that penetrates into the chemical 2. As is perhaps most clearly shown in FIG. 2, the elongated portion of each nozzle is closed at its upper end, as indicated by reference numeral 6*b*. The elongated portions and closed upper ends 6*b* of the nozzles are perforated by a plurality of peripheral bores 6*c* through which the regenerated air flows. From the interiors of the nozzles, the regenerated air exits through openings provided in short impermeable portions at lower ends of the nozzles that project from the cartridge casing and are connected to the respirator bag 7**.

According to the present invention, the peripheral surfaces 6a of the nozzles, including their closed ends 6b, are everywhere equidistant or substantially equidistant from the inlet surface 4 defined by end face 4a and generated surface 4b through which the user's exhaled air passes into the chemical 2. This construction and arrangement ensures that all regions, including edge regions, of the volume occupied by the chemical mass are flowed through and contacted by exhaled air so as to realize complete utilization of the chemical for oxygen production purposes. Moreover, since the respiratory air passes only once through the chemical 2 due to the cooperation of exhaled air valve 12 and inhaled air valve 13, the air is only moderately heated by the heat of reaction. Hence, the inhaled air, upon passing through the heat exchanger 14, reaches the user at a relatively low and comfortable breathing temperature.

To obtain advantageous flow conditions for the air passed through the space occupied by the chemical 2, it has been found preferable that the ratio of the area of surfaces 4a and 4b (which define the flow area of the incoming air exhaled by the user) to the area of surfaces 6a, as limited by the total area of bores 6c (which define the flow area of the outgoing air inhaled by the user), be between about 1:0.125 and 1:0.150. By virtue of incoming flow occurring over a relatively large area (inlet surface 4) and outgoing flow occurring over a relatively small area (the perforated areas of the two nozzles 6), as well as by placement of the peripheral surfaces 6a of the nozzles substantially equidistant from the inlet surface 4, throttled and, therefore, uniform flow is achieved through the entire space occupied by the chemical 2.

It is also desirable that an oxygen-yielding starting means 8, e.g., a chlorate plug or the like, be disposed on the base surface 1a of cartridge 1. Thus, when the plug is ignited, it can provide the initial requirement of oxygen to be discharged into the respirator bag 7.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A chemical cartridge for respirators comprising:

a casing;

a chemical mass within said casing which combines with carbon dioxide and water vapor and yields oxygen, said chemical mass being disposed in an insert formed of screen material, said insert spatially defining said chemical mass by an inlet surface comprising an end face and a generated circumferential surface;

a duct formed between inner walls of said casing and the entirety of said inlet surface; and a plurality of discharge nozzles comprising elongated portions projecting into said chemical mass, said nozzles being closed at first ends thereof and open at second ends thereof whereby exhaled air from a user that passes through said duct and said inlet surface into said chemical mass flows out of said second ends of said nozzles, said nozzles having perforated peripheral surfaces at said elongated portions and at said closed ends that are everywhere substantially equidistant from said inlet surface.

2. A chemical cartridge according to claim 1 wherein the ratio of the area of said inlet surface to an outflow area through said peripheral surfaces is between about 1:0.125 and 1:0.150.

3. A chemical cartridge according to claims 1 or 2 wherein said nozzles comprise elongated portions penetrating into said chemical mass, said elongated portions and said closed ends being perforated by a plurality of bores.

4. A chemical cartridge according to claim 1 wherein said nozzles include short portions projecting from said casing and connected to a respirator bag.

5. A chemical cartridge according to claim 1 wherein said nozzles are disposed on a base surface of said casing.

6. A chemical cartridge according to claim 1 wherein an oxygen-yielding starting plug is disposed in a substantially central region of a base surface of said casing.

7. A chemical cartridge according to claim 1 wherein said plurality of nozzles consists of two nozzles.

* * * * *